United States Patent [19]

Cummings

[11] Patent Number: 5,413,432
[45] Date of Patent: May 9, 1995

[54] MULTIPURPOSE PROCESSING SYSTEM AND METHOD FOR THE BENEFICIAL USE AND MANAGEMENT OF SLUDGE

[75] Inventor: James B. Cummings, Pittsburgh, Pa.

[73] Assignee: Chambers Development Co., Inc., Pittsburgh, Pa.

[21] Appl. No.: 194,815

[22] Filed: Feb. 14, 1994

Related U.S. Application Data

[63] Continuation of Ser. No. 947,052, Sep. 18, 1992, abandoned.

[51] Int. Cl.⁶ ............................................. B09B 1/00
[52] U.S. Cl. ................................... 405/129; 71/903; 241/DIG. 38; 405/128
[58] Field of Search ............... 405/128, 129; 71/12, 71/25, 30, 903; 241/19, DIG. 38

[56] References Cited

U.S. PATENT DOCUMENTS

| | | | |
|---|---|---|---|
| 4,016,073 | 4/1977 | Jordan | 405/129 X |
| 4,056,380 | 11/1977 | Thiac | 71/903 X |
| 4,323,367 | 4/1982 | Ghosh | 405/129 X |
| 4,469,176 | 9/1984 | Zison et al. | 405/129 X |
| 4,518,399 | 5/1985 | Croskell et al. | 405/129 X |
| 4,643,111 | 2/1987 | Jones | 405/129 X |
| 4,670,148 | 6/1987 | Schneider | 405/129 X |
| 4,834,300 | 5/1989 | Wojciechowski et al. | 405/129 X |
| 4,874,134 | 10/1989 | Wiens | 241/19 |
| 4,877,531 | 10/1989 | Burkett | 71/12 X |
| 4,925,571 | 5/1990 | Jacob et al. | 71/903 X |
| 4,931,192 | 6/1990 | Covington et al. | 405/129 X |
| 4,997,572 | 3/1991 | Wurtz | 71/903 X |
| 5,069,801 | 12/1991 | Girovich | 71/12 X |
| 5,252,116 | 10/1993 | Markham et al. | 71/25 X |
| 5,253,467 | 10/1993 | Sims | 56/372 |

FOREIGN PATENT DOCUMENTS 3300464 7/1984 Germany .................. 405/129

OTHER PUBLICATIONS

Using Compacted Garbage in Landfill Washington Post, May 25, 1973, p. D12.

*Primary Examiner*—Dennis L. Taylor
*Attorney, Agent, or Firm*—Ansel M. Schwartz

[57] ABSTRACT

The present invention pertains to a landfill and sludge processing system. The landfill system comprises a first facility for disposing sludge with waste in a landfill, a second facility for forming a compost pile of yard waste mixed with sludge, a third facility for pelletizing sludge for ultimate use as a fuel, and a fourth facility for processing sludge for use in land enhancement applications. Preferably, there is a generator facility for producing energy from the pelletized sludge. The present invention is also comprised of a method for operating a landfill system. As shown in flow chart form in FIG. 6, the method includes the steps of transporting sludge to the landfill system disposing a first portion of the sludge with waste in a landfill, disposing a second portion of the sludge with yard waste to form a compost pile, forming a third portion of the sludge into pellets for ultimate use as a fuel and processing a fourth portion of the sludge for land enhancement applications. Preferably, there is the step of collecting gas produced in the landfill of sludge and waste. Preferably, after the collecting step, there is the step of generating energy by burning the gas.

11 Claims, 4 Drawing Sheets

MULTIPURPOSE PROCESSING SYSTEM AND METHOD FOR THE BENEFICIAL USE AND MANAGEMENT OF SLUDGE

This is a continuation of application Ser. No. 07/947,052 filed on Sep. 18, 1992, now abandoned.

FIELD OF THE INVENTION

The present invention relates to landfills and processing facilities. More specifically, the present invention relates to a system and method wherein sludge is managed and used and processed for a variety of beneficial purposes.

BACKGROUND OF THE INVENTION

The disposal of human waste is becoming a matter of increasing concern in today's society. It is no longer a sole objective of waste management to bury waste without regard for its potential uses. For instance, sludge, which is an end product of the processing of sewage, represents a valuable source of organic matter. Sludge can be used for a variety of beneficial purposes, such as for the production of organic compost, for burning as a fuel or for the increased production of gas in a landfill which can then be used for electrical energy creation. Currently, only a fraction of disposed sludge is used for beneficial purposes. Part of the reason for this problem is that currently there are few facilities specifically adapted to use sludge in a beneficial manner.

The present invention provides a landfill system and method in which sludge is used for a variety of useful and beneficial purposes.

SUMMARY OF THIS INVENTION

The present invention pertains to a landfill system. The landfill system comprises a first facility for disposing sludge with waste in a landfill, a second facility for forming a compost pile of yard waste mixed with sludge, a third facility for pelletizing sludge for ultimate use as a fuel, and a fourth facility for processing sludge for use in land enhancement applications. Preferably, there is a generator facility for producing energy from the pelletized sludge.

The present invention is also a method for operating a landfill system. The method includes the steps of transporting sludge to the landfill system, disposing a first portion of the sludge with waste in a landfill, disposing a second portion of the sludge with yard waste to form a compost pile, forming a third portion of the sludge into pellets for ultimate use as a fuel and processing a fourth portion of the sludge for land enhancement applications. Preferably, there is the step of collecting gas produced in the landfill of sludge and waste. Preferably, after the collecting step, there is the step of generating energy by burning the collected gas.

BRIEF DESCRIPTION OF THE DRAWINGS

In the accompanying drawings, the preferred embodiment of the invention and preferred methods of practicing the invention are illustrated in which.

DESCRIPTION OF THE PREFERRED EMBODIMENT

Figure 5:
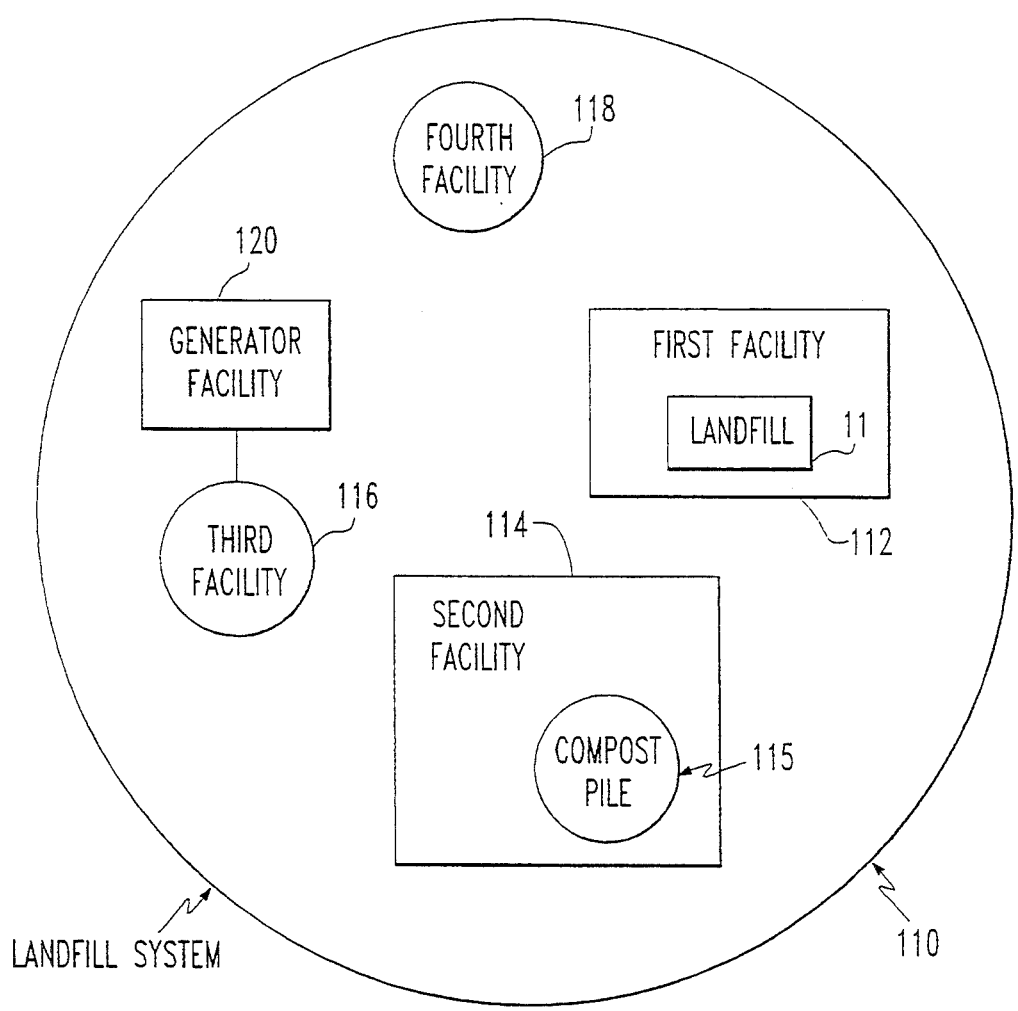
FIG. 5 is a schematic representation of a landfill system.

Referring now to the drawings wherein like reference numerals refer to similar or identical parts throughout the several views, and more specifically to FIG. 5 thereof, there is shown a landfill system 110. The landfill system 110 comprises a first facility 112 for disposing sludge 15 with waste 13 in a landfill 11, a second facility 114 for forming a compost pile 115 of yard waste mixed with sludge 15, a third facility 116 for pelletizing sludge 15 for ultimate use as a fuel, and a fourth facility 118 for processing sludge 15 for use in land enhancement applications. Preferably, there is a generator facility 120 for producing energy from the pelletized sludge.

Figure 6:
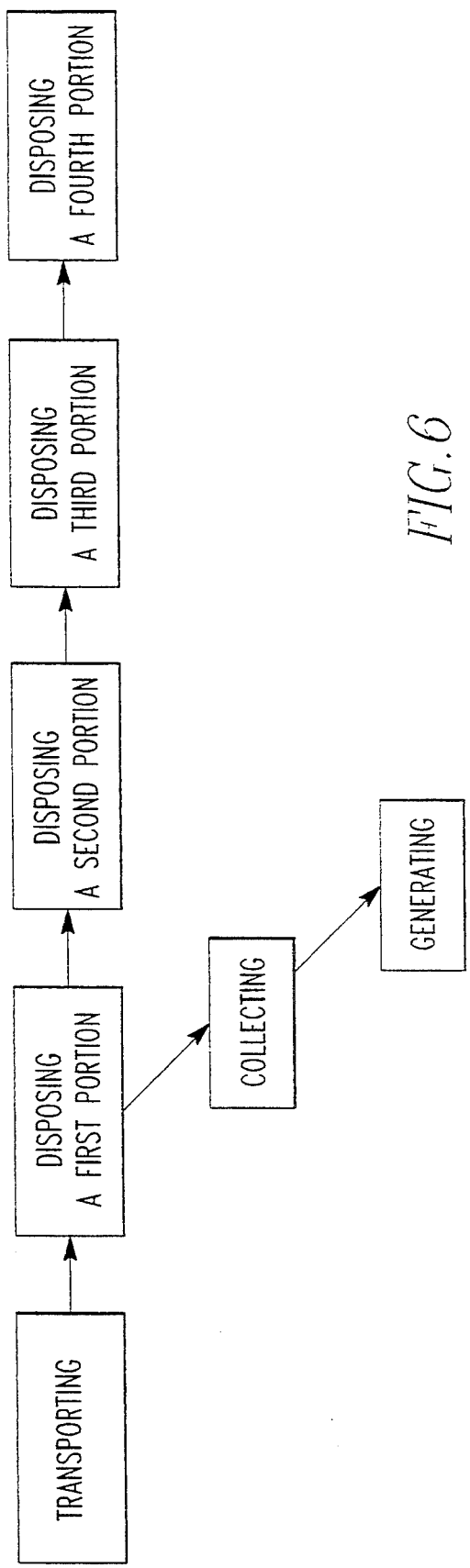
FIG. 6 is a flow chart of a method for operating a landfill system.

The present invention is also comprised of a method for operating a landfill system. As shown in flow chart form in FIG. 6, the method includes the steps of transporting sludge 15 to the landfill system 110, disposing a first portion of the sludge 15 with waste 13 in a landfill 11, disposing a second portion of the sludge 15 with yard waste to form a compost pile 115, forming a third portion of the sludge 15 into pellets for ultimate use as a fuel and processing a fourth portion of the sludge 15 for land enhancement applications. Preferably, there is the step of collecting gas produced in the landfill of sludge 15 and waste 13. Preferably, after the collecting step, there is the step of generating energy by burning the gas.

With reference to the first facility 112, the addition of sludge 15 to waste 13 in a landfill 11 produces high rates of methane production. Methane is generated as a product of anaerobic decomposition by methanogenic bacteria. Anaerobic decomposition occurs in almost all organic compounds, with few exceptions, oxidized by the action of strong oxidizing agents under acid conditions. The following formula (1) represents the chemical reactions occurring in anaerobic decompositions.

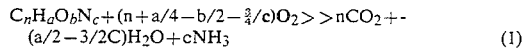
$$C_nH_aO_bN_c + (n + a/4 - b/2 - \tfrac{3}{4}c)O_2 \gg nCO_2 + (a/2 - 3/2C)H_2O + cNH_3 \qquad (1)$$

The sludge 15 increases the chemical reaction rate and thus, as a result of anaerobic decomposition, increases methane production by adding methanogenic bacteria (producers) to the waste 13 and the sludge 15 provides high levels of volatile acids which act as a fuel source for the methanogenic bacteria. For a more detailed explanation of the methane production of sludge waste mixtures, see Stamm et al. "Demonstration of Landfill Gas Enhancement Techniques in Landfill Simulators" Eighth Annual Madison Waste Conference, University of Wisconsin-Madison, (1985), or Stamm et al "Evaluation of the Impacts of Sludge Landfilling" Eighth Annual Madison Waste Conference, University of Wisconsin-Madison, (1985).

Figure 1:
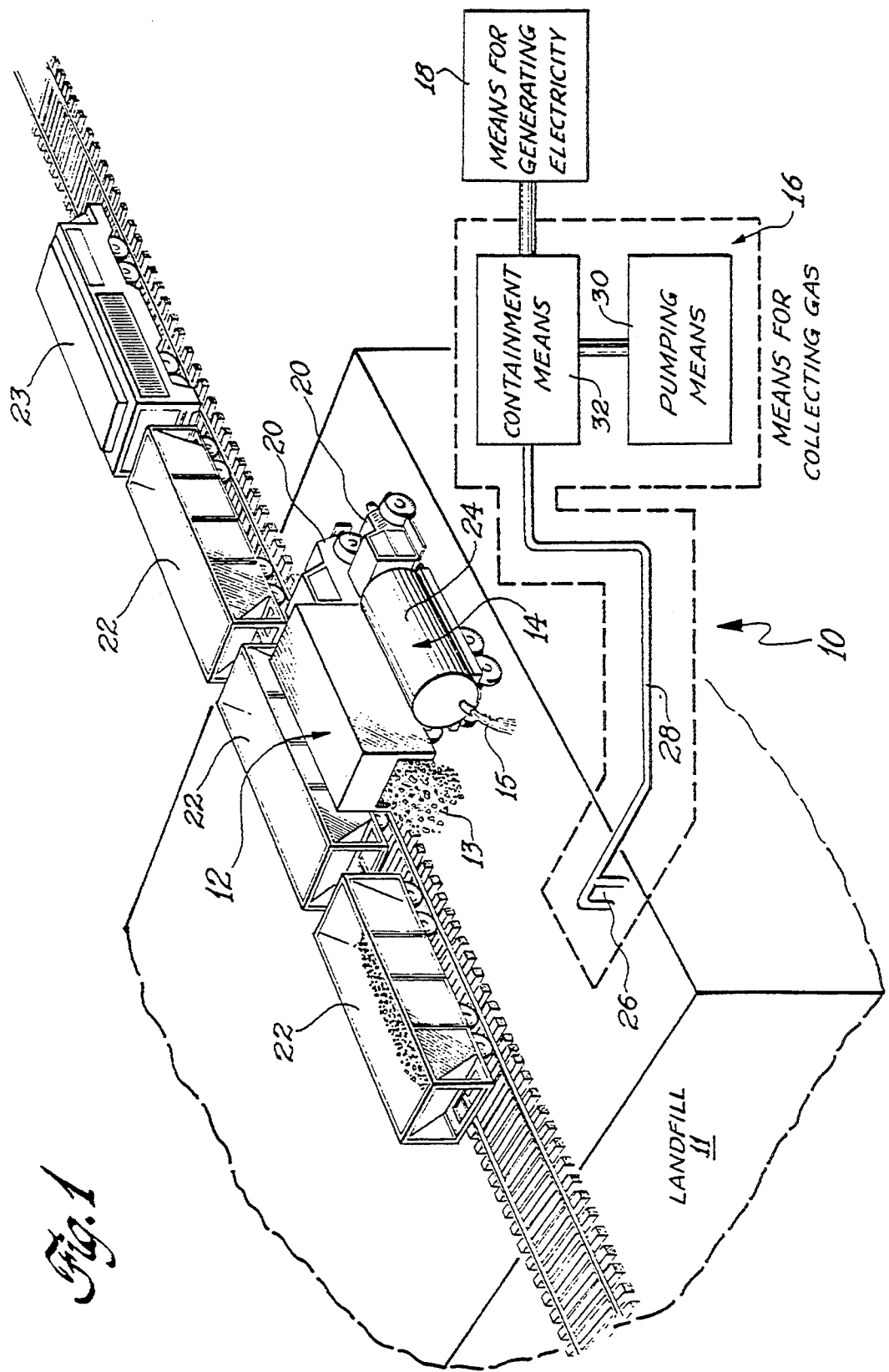
FIG. 1 is a schematic representation showing a gas-to-energy system of the present invention.

Preferably, as shown in FIG. 1, the first facility 112 comprises a gas-to-energy system 10. The system 10 is comprised of means 12 for disposing waste 13 in the landfill 11 and means 14 for disposing sludge 15 in the landfill with the waste 13. The system 10 also includes means 16 for collecting gas produced within the landfill from the sludge 15 mixed with the waste 13 and means 18 for generating electricity from the collected gas, such as methane. The generating means 18 is in fluidic communication with the collecting means 16. Preferably, the generating means 18 includes an electrical generator which burns the gas to produce electricity.

Preferably, the means 12 for disposing the waste 13 in the landfill includes at least one truck 20 and/or at least one railroad car 22 of a train 23. Preferably, the means 14 for disposing sludge 15 in the landfill includes at least one sealable or covered container 24 which can also be transported by truck 20 or train 23.

In a preferred embodiment, the gas collecting means includes a plurality of gas extraction wells 26 located throughout the landfill 11, a piping network 28 connected to the extraction wells 26, pumping means 30 for moving gas produced within the landfill 11 into the piping network 28 and containment means 32 in communication with the piping network 28 for storing collected gas.

Figure 2:
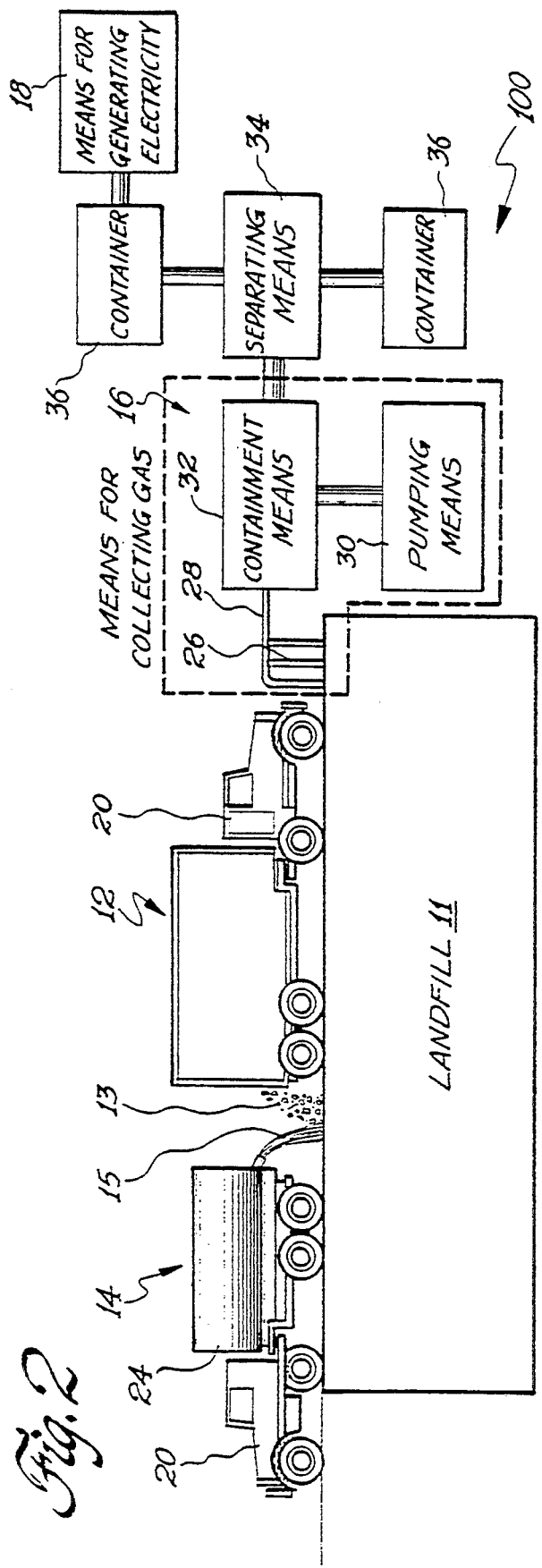
FIG. 2 is a schematic representation showing a preferred embodiment of a gas-to-energy system of the present invention.

In another embodiment and as shown in FIG. 2, the first facility 112 can include a system 100 for a landfill 11. The system 100 comprises means 12 for disposing waste 13 in the landfill 11 and means 14 for disposing sludge 15 in the landfill 11 with the waste 13. The system 100 is also comprised of means 16 for collecting gas produced within the landfill 11 from the sludge 15 mixed with the waste 13 and means 34 for separating the gas into components having a common molecular structure. The separating means 34 is in communication with the collecting means 16. There is also a plurality of containers 36 for containing the components. The containers 36 are in communication with the separating means 34.

In a preferred embodiment, the system 100 includes means 18 for generating electricity from combustible components of the gas such as methane. The generating means 18 is in communication with the containers 36. The collecting means 16 can include a plurality of gas extraction wells 26 located throughout the landfill, a piping network 28 connected to the extraction wells 26, pumping means 30 for moving gas produced within the landfill 11 into the piping network 28 and containment means 32 in communication with the piping network 28 for storing collected gas.

Figure 3:
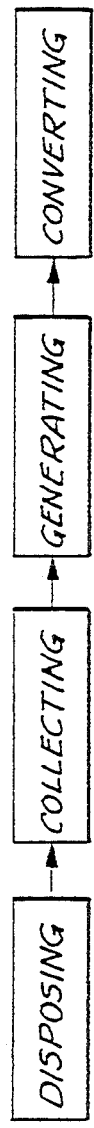
FIG. 3 is a flow chart of a first method of operating a landfill.

As shown in FIG. 3, the present invention is also a method of operating a landfill 11. The method is characterized by the step of disposing sludge 15 in the landfill 11 having waste 13 to form a sludge/waste mixture such that gas production of the sludge/waste mixture during decomposition is greater than gas production that would have resulted during decomposition of the waste only. Then, there is the step of collecting the gas produced by the sludge/waste mixture. Next, there is the step of generating energy by burning the gas. Then, there is the step of converting the energy into work. The work can be mechanical work or electrical work. Preferably, the generating energy step includes the step of generating electricity and the converting step includes the step of converting the electricity into work. Preferably, after the collecting step, there is the step of transferring the gas into a container and the generating step includes the step of burning the gas at a location remote from the landfill. For instance, the gas, such as methane, can be collected, redistributed and used for fuel for methane burning motor vehicles. See "Sludge/Waste Landfill Method and System" having Ser. No. 07/947,045 filed on the same day as this patent application, incorporated by reference.

Figure 4:
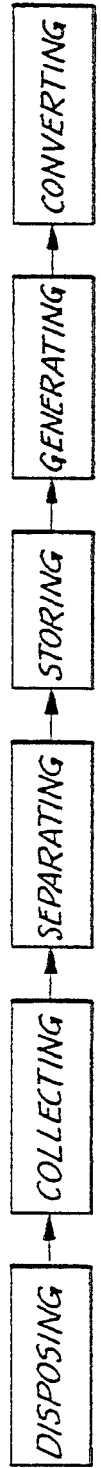
FIG. 4 is a flow chart of a second method of operating a landfill.

As shown in FIG. 4, the present invention is also a method of operating a landfill 11 comprised of the steps of disposing sludge 15 in a landfill 11 having waste 13 to form a sludge/waste mixture such that gas production of the sludge/waste mixture during decomposition is greater than gas production that would have resulted during decomposition of the waste only. Then, there is the step of collecting the gas produced by the sludge/waste mixture. Next, there is the step of separating the gas into components having a common molecular structure. Then, there is the step of storing each of the components into separate containers.

Preferably, after the storing step, there is the step of transporting the containers to a predetermined location. Preferably, after the storing step, there are the steps of generating energy by burning combustible components of the gas and converting the energy into work. The combustible components of the gas can be methane, for instance.

An example of where sludge is combined with municipal waste in a landfill is the Charles City County landfill site of Charles City, Va. A ratio of 5 parts municipal waste to 1 part sludge is used at the Charles City County landfill site.

An example of where methane gas is collected in an extraction system of a landfill site is the Monroeville landfill site in Monroeville, Pa. The extraction system collects the methane gas and directs it to an expulsion point where it is flared.

An example of a landfill site that gathers methane gas for the production of electricity is the Puente Hills Energy Recovery Site in Los Angeles, Calif. At the Puente Hills energy recovering site, the extraction system collects methane gas and directs it to a gas fired power plant where the gas is burned to operate the engines to produce electricity.

With respect to the in the operation of the invention, the landfill area 11 of the first facility 112 is created by known techniques. Municipal waste 13 is then transported to the landfill area 11 with tractor trailers or like transportation devices 20 where it is disposed in the landfill area 11 in piles. The sludge 15 is transported by truck or rail in sealed or covered containers 24 to the landfill area 11. The sludge 15 is also disposed in the landfill area 11 in piles adjacent to the waste piles 13. Computerized tracking at the entrance gate of the landfill 11 verifies that transportation vehicles are bringing five parts waste 13 to one part sludge 13 into the landfill area 11 during the disposing process. That is, five tons of waste 13 to one ton of sludge 15 are allowed into the landfill area 11.

Compactors are then used to mix the piles of waste 13 with the piles of sludge 15 and to distribute the waste/sludge mixture in the landfill area 11. As a general rule, the drivers of the bulldozers are told to mix ten parts waste per volume with one part sludge per volume since this ratio is roughly equivalent to the desired 5 to 1 waste/sludge ratio in terms of mass.

The liquid content of the five to one waste/sludge ratio in terms of mass is appropriate for five reasons. First, a five to one waste/sludge mixture results in greater methane production than waste 13 only. Second, a five to one waste/sludge mixture avoids leachate problems by too much liquid accumulating in one area. Third, a five to one waste/mixture is stable enough to be formed into piles. If greater amounts of sludge 15 is mixed with the waste 13, the resulting mixture has too much liquid to hold an appropriate form and any mounds of the mixture collapse. Fourth, the five to one waste/sludge mixture prevents sinkholes and potholes from forming over time in the landfill area 11 as the sludge 15 settles, dries and decays. Fifth, a five to one waste/sludge mixture avoids traffic problems within the landfill. If a greater ratio of sludge 15 is mixed with the waste 13, then the landfill area 11 becomes too fluidic for transportation by the trucks of sludge or waste because they become stuck in the surface material.

It should be noted that alternative procedures for placing sludge and municipal waste in a landfill can be accommodated. For instance, layers of sludge 15 and waste 13 can be placed on top of each other. Also, the ratio of waste/sludge can, for instance, be one to one or one hundred to one or any ratio in between. In general, by varying the ratio of sludge 15 to waste 13 the quantity of methane per unit of time can be controlled. For instance, by placing a large amount of sludge in a short period of time in contact with the waste 13, production of methane for a given unit of time is greatly increased until the active sludge/waste relationship becomes neutralized.

Once the landfill area 11 is filled with five parts waste 13 to one part sludge 15 per mass, it is covered as is known in the art. Note the entire landfill area 11 does not need to be filled before covering can commence. A gas collection system 16 is then installed within the landfill area 11 in a phased sequence since methane production does not occur immediately but after a period of time has passed when the sludge 15 and waste 13 are mixed. The collection system 16 is comprised of a plurality of gas extraction wells 26 located throughout the landfill 11, a piping network 28 connected to the extraction wells 26 and a pump 30 for creating a vacuum within the piping network 28 to pull gas emitted by the decomposing waste/sludge mixture into the extraction wells 26. The gas collected by the collection system 16 is moved into containment means 32 for storage or separation. As is well known, the collected gas typically consists of large parts of methane. This methane is a valuable source of energy. The methane gas can be burned directly at the landfill facility, such as in reciprocating engines, to produce electricity or can be transported in containers to a central distribution facility, such as a gas station, for ultimate transferral to the fuel tanks of methane burning vehicles, such as automobiles. In this manner, the by-products of the decomposing waste/sludge mixture can be used as an energy source either at the landfill site 11 or remote from the landfill site 11. Further, it should be appreciated that noncombustible components of the collected gas, such as $CO_2$, can be separated out from the methane and stored in a separate container 36. The $CO_2$ can then be sold to the appropriate vendors.

With respect to the operation of the second facility 114, sludge 15 is mixed with yard waste, such as grass clippings and leaves. Bulldozers mix the sludge and yard waste and push the mixture into at least one compost pile 115. As the yard waste is primarily organic, the sludge 15 and yard waste over time will break down into a nutrient rich mixture, which, as is well known, can be used as a fertilizer. The compost can be packaged and sold, for instance, thereby allowing beneficial use of sludge.

With respect to the operation of the third facility 116 sludge is processed through a mechanical system which results in the pelletization of sludge 15 for ultimate use as a fuel.

With respect to the operation of the fourth facility 120, sludge 15 is processed through a mechanical system which results in a sludge product suitable for land applications including but not limited to uses involving landfill daily cover.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A landfill system comprising:
   a first facility for disposing sludge with waste in a landfill;
   a second facility for forming a compost pile of yard waste mixed with sludge;
   a third facility for pelletizing sludge for ultimate use as a fuel;
   a fourth facility for processing sludge for use in land enhancement applications, said first, second, third and fourth facilities located within a common landfill area; and
   means for transporting a portion of sludge brought to the landfill to each of the first, second, third and fourth facilities, said transporting means disposed in said landfill and in communication with each of the first, second, third and fourth facilities, said transporting means including means for disposing sludge in the landfill with the waste during formation of the landfill and wherein the first facility includes means for collecting gas produced within the landfill from the sludge mixed with the waste directly from the landfill, a piping network connected to the collecting means through which gas from the landfill is channeled, and means for generating electricity from the collected gas, said generating means in fluidic connection with the collecting means through the piping network such that gas collected directly from the landfill is channeled to the generating means.

2. A landfill system as described in claim 1 including a generator facility for producing energy from the pelletized sludge.

3. A method for operating a landfill system comprising the steps of:
   transporting sludge to the landfill;
   disposing a first portion of the sludge with waste in a landfill;
   generating energy from gas produced from sludge and waste from the first portion of sludge with waste;
   disposing a second portion of the sludge with yard waste to form a compost pile;
   forming a third portion of the sludge into pellets for ultimate use as a fuel;
   processing a fourth portion of the sludge for land enhancement applications wherein the waste is disposed at a first facility in the landfill, the compost pile is disposed at a second facility in the landfill, the formation of the pellets is at a third facility in the landfill, and the processing of the fourth portion of the sludge is at a fourth facility in the landfill; and providing the energy to the second, third and fourth facilities to power them, said second third and fourth facilities connected to the first facility to receive the energy.

4. A method as described in claim 3 including the step of collecting gas produced in the landfill of sludge and waste.

5. A method as described in claim 4 wherein after the collecting step, there is the step of generating energy by burning the collected gas.

6. A method as described in claim 4 wherein the step of disposing a first portion of the sludge with waste in a landfill includes the step of mixing five parts waste with one part sludge to form a five to one waste/sludge ration in terms of mass.

7. A system as described in claim 1 wherein the transporting means includes a truck.

8. A system as described in claim 1 wherein the transporting means includes a railroad.

9. A landfill system comprising:
 a first facility for disposing sludge with waste in a landfill and generating energy from gas produced from the sludge and waste;
 a second facility for forming a compost pile of yard waste mixed with sludge, said second facility powered from the energy produced by the first facility, said second facility connected to the first facility to receive the energy;
 a third facility for pelletizing sludge for ultimate use as a fuel, said third facility powered from the energy produced by the first facility, said third facility connected to the first facility to receive the energy;
 a fourth facility for processing sludge for use in land enhancement applications, said fourth facility powered from the energy produced by the first facility, said fourth facility connected to the first facility to receive the energy, said first, second, third and fourth facilities located within a common landfill area; and
 means for transporting a portion of sludge brought to the landfill to each of the first, second, third and fourth facilities, said transporting means disposed in said landfill and in communication with each of the first, second, third and fourth facilities, said transporting means including means for disposing sludge in the landfill with the waste during formation of the landfill and wherein the first facility includes means for collecting gas produced within the landfill from the sludge mixed with the waste directly from the landfill, a piping network connected to the collecting means through which gas from the landfill is channeled, and means for generating electricity from the collected gas, said generating means in fluidic connection with the collecting means through the piping network such that gas collected directly from the landfill is channeled to the generating means.

10. A system as described in claim 9 wherein the transporting means includes a truck.

11. A system as described in claim 9 wherein the transporting means includes a railroad.

* * * * *